(12) United States Patent
Katou

(10) Patent No.: US 8,968,304 B2
(45) Date of Patent: Mar. 3, 2015

(54) MEDICAL DEVICE

(75) Inventor: Yukitoshi Katou, Hatanoshi (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 380 days.

(21) Appl. No.: 13/587,511

(22) Filed: Aug. 16, 2012

(65) Prior Publication Data

US 2012/0310227 A1 Dec. 6, 2012

Related U.S. Application Data

(63) Continuation of application No. PCT/JP2011/050264, filed on Jan. 11, 2012.

(30) Foreign Application Priority Data

Mar. 11, 2010 (JP) .................................. 2010-054847

(51) Int. Cl.
*A61B 18/18* (2006.01)
*A61B 18/12* (2006.01)
*A61B 18/14* (2006.01)
(Continued)

(52) U.S. Cl.
CPC ......... *A61B 18/1233* (2013.01); *A61B 18/1492* (2013.01); *A61B 18/1815* (2013.01); *A61B 18/20* (2013.01); *A61B 2018/00351* (2013.01); *A61B 2018/1861* (2013.01); *A61B 18/1477* (2013.01);
(Continued)

(58) Field of Classification Search
USPC ........................................................ 606/50
See application file for complete search history.

(56) References Cited

U.S. PATENT DOCUMENTS

| 6,122,549 A | 9/2000 | Sharkey et al. |
| 2002/0165536 A1 | 11/2002 | Kelley et al. |

(Continued)

FOREIGN PATENT DOCUMENTS

| EP | 0 876 804 A1 | 11/1998 |
| JP | 60-21185 U | 2/1985 |

(Continued)

OTHER PUBLICATIONS

Extended European Search Report issued Jul. 22, 2013, by the European Patent Office in corresponding European Patent Application No. 11753073.3 (6 pages).

(Continued)

*Primary Examiner* — Robert N Wieland
(74) *Attorney, Agent, or Firm* — Buchanan Ingersoll & Rooney PC

(57) ABSTRACT

A medical device includes a steering unit at a proximal portion of a catheter to steer operations of a heating unit at a distal portion of the catheter. The steering unit includes a main body portion interlocked with the catheter; a slide portion interlocked with the heating unit and slidable relative to the main body portion; a guide unit interlocked with the main body portion and fixed to the slide portion for movement therewith; and an input connector electrically connected with the heating unit and connectable with an output connector for supplying electric energy to the heating unit. The guide unit hinders connection between the input connector and the output connector. A cutout portion enables connection between the input and output connectors when the guide unit moves with respect to the main body portion and the heating unit moves to a position at which the biological tissue is heatable.

19 Claims, 18 Drawing Sheets

(51) Int. Cl.
*A61B 18/20* (2006.01)
*A61B 18/00* (2006.01)

(52) U.S. Cl.
CPC .................... *A61B 2018/0063* (2013.01); *A61B 2018/00916* (2013.01); *A61B 2018/143* (2013.01)
USPC .......................................................... 606/50

(56) References Cited

U.S. PATENT DOCUMENTS

| | | | |
|---|---|---|---|
| 2004/0230185 A1* | 11/2004 | Malecki et al. | 606/2 |
| 2005/0015048 A1 | 1/2005 | Chiu et al. | |
| 2005/0192626 A1 | 9/2005 | Widomski et al. | |
| 2009/0069810 A1 | 3/2009 | Kuroda et al. | |
| 2009/0118729 A1 | 5/2009 | Auth et al. | |
| 2010/0152732 A1 | 6/2010 | Katou | |

FOREIGN PATENT DOCUMENTS

| | | |
|---|---|---|
| JP | 62-039333 Y2 | 10/1987 |
| JP | 2-304880 A | 12/1990 |
| JP | 2007-519489 A | 7/2007 |
| JP | 2009-232878 A | 10/2009 |
| JP | 2009-233021 A | 10/2009 |
| WO | WO 2007/100067 A1 | 9/2007 |
| WO | 2009/028542 A1 | 3/2009 |

OTHER PUBLICATIONS

International Search Report (PCT/ISA/210) issued on Feb. 22, 2011, by the Japanese Patent Office as the International Searching Authority for International Application No. PCT/JP2011/050264.

* cited by examiner

MEDICAL DEVICE

CROSS-REFERENCES TO RELATED APPLICATIONS

This application is a continuation of International Application PCT/JP2011/050264 filed on Jan. 11, 2011, which claims priority to Japanese Patent Application No. 2010-054847 filed in Japan on Mar. 11, 2010, the entire content of both of which is hereby incorporated by reference.

TECHNICAL FIELD

This invention relates to a medical device for heat-treating a living body and, more particularly, to a hand-side steering unit for steering a medical device for heat-treating a living body.

BACKGROUND DISCUSSION

A medical treatment device for treating a patent foramen ovale (hereinafter, referred to as a PFO) has been described in International Publication No. WO2007/100067, the contents of which are hereby incorporated by reference. A PFO is a cardiogenic factor of a stroke and a migraine headache.

The PFO closing device described in International Publication No. WO2007/100067 includes an apparatus which is inserted into the foramen ovale from the right atrium toward the left atrium. A foramen ovale valve is pulled so as to close the foramen ovale, the foramen ovale valve and the atrial septum secundum are sandwiched by a pair of electrodes, and the biological tissue can then be fused by applying electric energy from both the electrodes.

In this device, clamping means are used in which one side thereof is made of a sticking member composed of a needle electrode and the other side thereof is made of a sandwiching member for sandwiching the foramen ovale valve and the atrial septum secundum with respect to the sticking member. The sticking member pierces (i.e., is stuck into) the foramen ovale valve and thereafter, the foramen ovale valve and the atrial septum secundum are sandwiched with respect to the sandwich member, which is the other electrode. Electric energy is applied to the biological tissue and fusion is thereby carried out.

This device can also be used in the case of closing defects such as a congenital atrial septum secundum defect (ASD), a ventricular septal defect (VSD) and a patent ductus arteriosus (PDA). The device has a high general versatility and in particular, foreign substances are not indwelled in the body. The construction of such a device is relatively simple, the procedure is easily performed, and the foramen ovale valve and the atrial septum secundum can be reliably fused.

However, when applying electric energy to the clamping means (in other words, to the electrode) which is exposed to blood, thrombi may easily attach to the clamping means. As such, it is not desirable for electric energy to be carelessly or needlessly applied to the electrodes for fusing the biological tissue.

SUMMARY

The medical device disclosed here includes a heating unit provided on a distal side of a catheter to heat a biological tissue and a hand-side steering unit provided at a proximal side of the catheter to steer advancement and retraction operations with respect to the catheter at the heating unit. The hand-side steering unit comprises a main body portion interlockable with the catheter; a slide portion which is interlockable with the heating unit and which is movable so as to approach and move backwards with respect to the main body portion; and a guide unit movably interlocked with one of the main body portion and the slide portion and fixed secured on the other one of the main body portion and the slide portion; an input connector provided at one of the main body portion, the slide portion and the guide unit, the input connector being electrically connected with the heating unit, and connectable with which an output connector, for supplying electric energy to the heating unit. One of the main body portion, the slide portion and the guide unit is disposed for hindering connection between the input connector and the output connector, said one of the main body portion, the slide portion or the guide unit which is disposed for hindering connection between the input connector and the output connector is different from said one of the main body portion, the slide portion and the guide unit which is provided with the input connector. Also included is a connection adjusting unit for enabling connection between the input connector and the output connector by moving the slide portion with respect to the main body portion when the heating unit is moved to a position at which the biological tissue is heatable.

BRIEF DESCRIPTION OF DRAWINGS

FIGS. 11A and 11B are plan views showing the hand-side steering unit in an operative position when a needle steering lever is steered, in which FIG. 11A shows a state before the steering and FIG. 11B shows a state after the steering.

FIGS. 12A and 12B are enlarged plan views showing the hand-side steering unit in an operative position when a slide portion is moved backward, in which FIG. 12A shows a state in the midst of the backward movement and FIG. 12B shows a state after the backward movement.

DETAILED DESCRIPTION

A medical device, such as a PFO closing device, will be explained below by reference to the exemplified embodiments described herein and as shown in the accompanying drawings.

Figure 1:
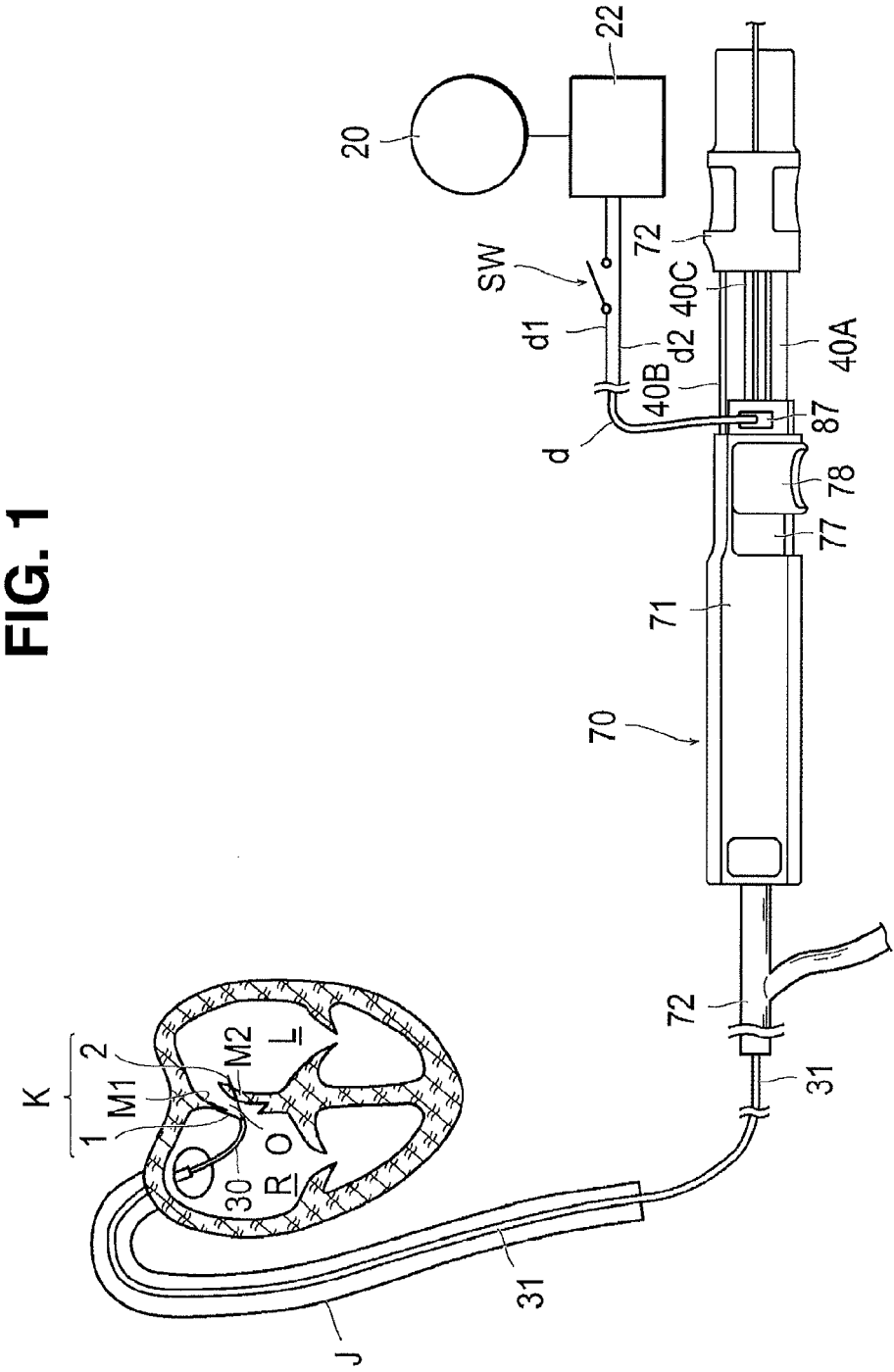
FIG. 1 is a schematic cross-sectional view showing a PFO closing device according to an embodiment disclosed here by way of example.
Figure 2:
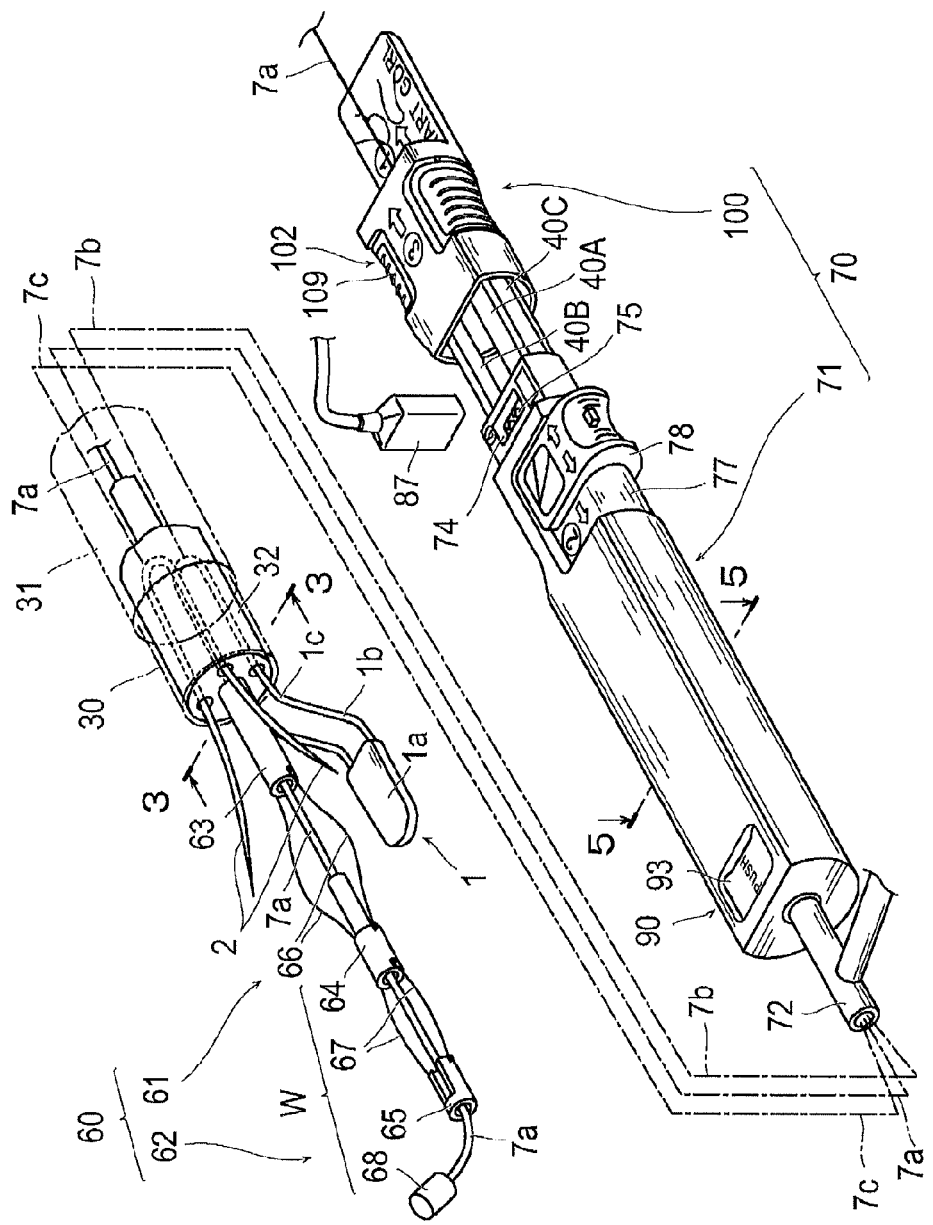
FIG. 2 is a perspective view of the main portion of the PFO closing device shown in FIG. 1.
Figure 3:
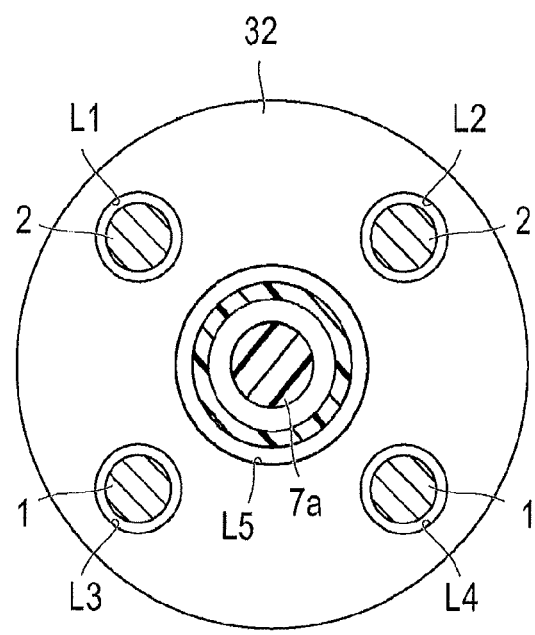
FIG. 3 is a cross-sectional view of a catheter distal portion taken along a line 3-3 as shown in FIG. 2.

With reference initially to FIGS. 1-3, the PFO closing device includes a hand-side steering unit 70 provided on the proximal side, a guiding catheter 31 whose proximal end is interlockable with the hand-side steering unit 70, a catheter 30 whose proximal end is attached to the hand-side steering unit 70 and which is provided in the guiding catheter 31, clamping means K which is provided at a distal portion of the catheter 30 and which sandwiches a foramen ovale valve M2 and an atrial septum secundum M1, energy supply means 20 for supplying electric energy which fuses or necrotizes a biological tissue M (generic term of M1, M2) of a portion sandwiched by the clamping means K, and positioning hold means 60 (see FIG. 2) for stably and accurately performing the surgical procedure with the clamping means K. As used in the following explanation, the hand-side steering unit 70 side of the device is referred to as a "proximal side" and the clamping means K side of the device is referred to as a "distal side".

When using the device, the guiding catheter 31 is first inserted, for example, from a femoral vein J. The guiding catheter 31 is inserted with the catheter 30, and the clamping means K provided at the distal end of the catheter 30, stored therein. After the distal end of the catheter 30 reaches the region of the heart at which the procedure is to be executed, the clamping means K is protruded from the catheter 30 by steering the hand-side steering unit 70. The tissues of the atrial septum secundum M1 and the foramen ovale valve M2 of the heart in which there is a defect O of a foramen ovale (hereinafter, sometimes referred to simply as foramen ovale O) are then sandwiched by the clamping means K. In this sandwiched state, the clamping means K is supplied with electric energy, both the tissues (M1 and M2) are heated and fused, and the defect O is closed. More specifically, the clamping means K functions as a heating unit. As shown, in FIG. 1, "L" denotes a left atrium and "R" denotes a right atrium.

The clamping means K comprises a sandwich member 1 directly contacting one side surface of the atrial septum secundum M1 and a sticking member 2 which is stuck into the foramen ovale valve M2. The sandwich member 1 includes, as shown in FIG. 2, a flat-plate portion 1a having an overall generally flat plate shape and a pair of wire portions 1b connected to the proximal portion thereof. The position of the flat surface of the flat-plate portion 1a is restricted by lumens L3, L4 (see FIG. 3) of a distal end tip 32 fixed at the distal end of the catheter 30. The sandwich member 1 is connected with one line of steering cord 7b on the proximal side of the U-shaped wire member portion 1b. By advancing and retracting the steering cord 7b in the axial direction, the sandwich member 1 protrudes from the distal end tip 32 and forms a predetermined sandwich width with respect to the sticking member 2. The sandwich member 1 is thereby displaced so as to sandwich the biological tissue M by approaching toward the sticking member 2 side when entering into the distal end tip 32.

The sticking member 2 is held by lumens L1, L2 (see FIG. 3) formed in the distal end tip 32 of catheter 30 so as to be movable forward and backward in a state in which the position of the flat surface thereof is restricted. The distal portion of the sticking member 2 is configured so as to be retractable from the distal end tip 32 by operating a steering cord 7c connected to the proximal side of the U-shaped sticking member 2.

The sticking member 2 has a certain elasticity such that two very fine needle-shaped members are mutually separated. A cross-section of each needle-shaped member taken perpendicular to the longitudinal axis is circular. The distal ends thereof are sharply pointed and are mutually separated and also open widely when protruded from the catheter. Also, although two needle members are shown in the illustrated embodiment, the number of needle members can be in one piece or three pieces or more.

The sandwich member 1 and the sticking member 2 both function as electrode members (heating units), and the steering cords 7b, 7c which operatively protrude and retract the sandwich member 1 and the sticking member 2 from the catheter 30 (see FIG. 2) are connected electrically with the energy supply means 20 through an input connector 75 which passes through the inside of the catheter 30 and is provided at the hand-side steering unit 70, an output connector 87 which is a plug fitted for connection to the input connector 75 (see FIG. 1), and a conduction wire d (common designation of d1, d2) connected with the electrode terminal of the output connector 87 and a control unit 22. Either one of the conductive wires d1, d2 (conductive wire d1 in this exemplified embodiment) is connected with a foot switch SW to be installed at the operator's feet in order to provide ON/OFF control the electric current from the energy supply means 20. As an alternative to the foot switch SW, a switch which can easily be operated on the hand-side steering unit could also be used.

The hand-side steering unit 70 is a unit for steering the clamping means K, comprised of a pair of electrode members which sandwich the biological tissue M lying in the vicinity of a defect existing in the biological tissue, such that the clamping means K is retractively protruded from the distal end of the catheter 30. The disclosure below describes means by way of example such that it is possible to carry out all operations within the small area of the defect without significant movement of a hand of the operator.

In other words, the hand-side steering unit 70 is provided, as shown in FIG. 2, with a needle steering lever 78 for steering the sticking member 2 which is one electrode member, a slide portion 100 for steering the sandwich member 1 which is the other electrode member, a main steering rod 7a which is a rod for assisting with the steering of the clamping means K and which movably passes in the axial direction through the inside of the hand-side steering unit 70 and the catheter 30, a pusher piece 109 which operates a lock/unlock mechanism 102 for locking/unlocking the slide movement of the slide portion 100 (see FIG. 9) and also locks the movement of the main steering rod 7a in the axial direction, and the input connector 75 which is provided with an electrode terminal to be connected with energy supply means 20 for applying thermal (electric) energy.

Figure 4:
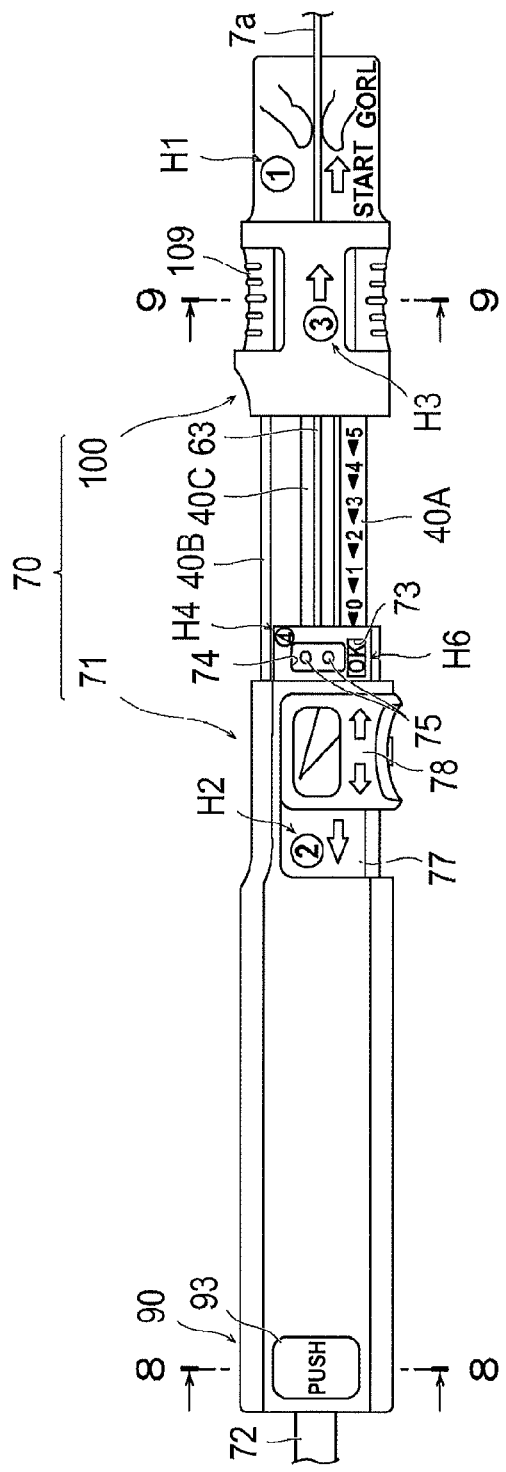
FIG. 4 is a plan view showing a hand-side steering unit of the PFO closing device shown in FIG. 1.
Figure 11:
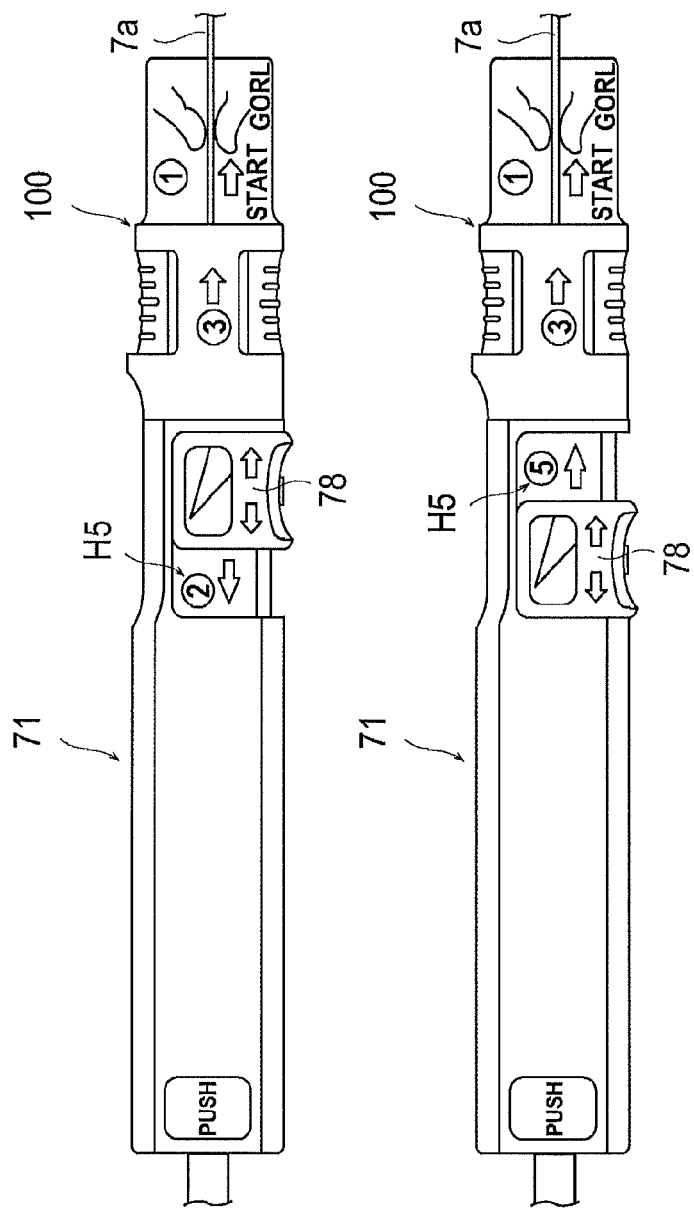

As shown in FIG. 4, the hand-side steering unit 70 is provided with a process indicating portion H (common designation of H1 to H5) in order to make processes in various kinds of procedures visible. The process indicating portion H is given various indications at the surface portion thereof for guiding the operator so as to carry out a correct operation (see FIG. 11B for the process indicating portion H5).

The process indicating portion H includes an indicating portion H1 for a rod traction process of operating the pusher piece 109 and exerting traction on the main steering rod 7a; an indicating portion H2 for a sticking process in which the sticking member 2 sticks the biological tissue; an indicating portion H3 for a slide portion movement process which moves the slide portion 100 slidingly and carries out sandwiching or release of the biological tissue; an indicating portion H4 for a connection process of connecting the input connector 75 with the energy supply means 20; and an indicating portion H5 (see FIG. 11B) for a sticking unit moving-back (retraction) process of moving the sticking member 2 backward from the biological tissue. Indications are provided for imaging respective processes by using graphic indications, numbers and/or arrows of movement directions respectively. In the process indicating portion H, the color by which each steering-member is colored and the color of the arrow indicating the movement direction of each steering-member are the same in order to make it easy to understand the steering of the steering-member.

In this manner, when a process indicating portion H is provided for the hand-side steering unit 70 and the orders and movement directions of various kinds of processes become visible, it is not necessary for the operator to be perfectly familiarized with the sequence of the processes beforehand. That is, the sequence can easily be understood by seeing the process indicating portion H. It is therefore possible to reduce the mental burden on the operator at the time of use and to smoothly and reliably carry out the procedure while also improving the safety of the processes. It is also possible for the process indicating portion H not only to make an indication by using graphic indication but also to make an indication in an itemization manner (i.e., numerical order) on the surface of the hand-side steering unit 70.

Note that with respect to the operation immediately before carrying out the energy connection process, not only is the procedure of sandwiching the biological tissue with the clamping means K employed, but there may also be other procedures employed beforehand. In other medical devices, for example, there may be various other kinds of procedures employed immediately before carrying out a connection between the energy supply means 20 and the input connector 75, and this exemplified embodiment is also applicable to such other medical devices.

With relation to the needle steering lever 78, when moving the sticking member 2 in the sticking direction (from the state shown in FIG. 11A to the state shown in FIG. 11B), the needle steering lever 78 is configured such that there appears an indication of the subsequent moving direction and a number indicating the order of the operation process from the lower surface of the needle steering lever 78. In this manner, a fool proof function, in other words a safety function, is designed so as not to create a dangerous situation even if the operator carries out an erroneous operation. This safety function increases the reliability and safety of the procedure.

Further, for purposes of explaining the hand-side steering unit 70 in greater detail, the hand-side steering unit 70 includes, as shown in FIG. 2, a main body portion 71 on the side to which the guiding catheter 31 is interlocked and a slide portion 100 which is interlocked with the proximal side of the main body portion 71 through guide bars (guide units) 40A, 40B, 40C for movement toward and away from the main body portion 71. On the upper surface of the main body portion 71, the needle steering lever 78 is provided which steers the sticking member 2.

Figure 5:
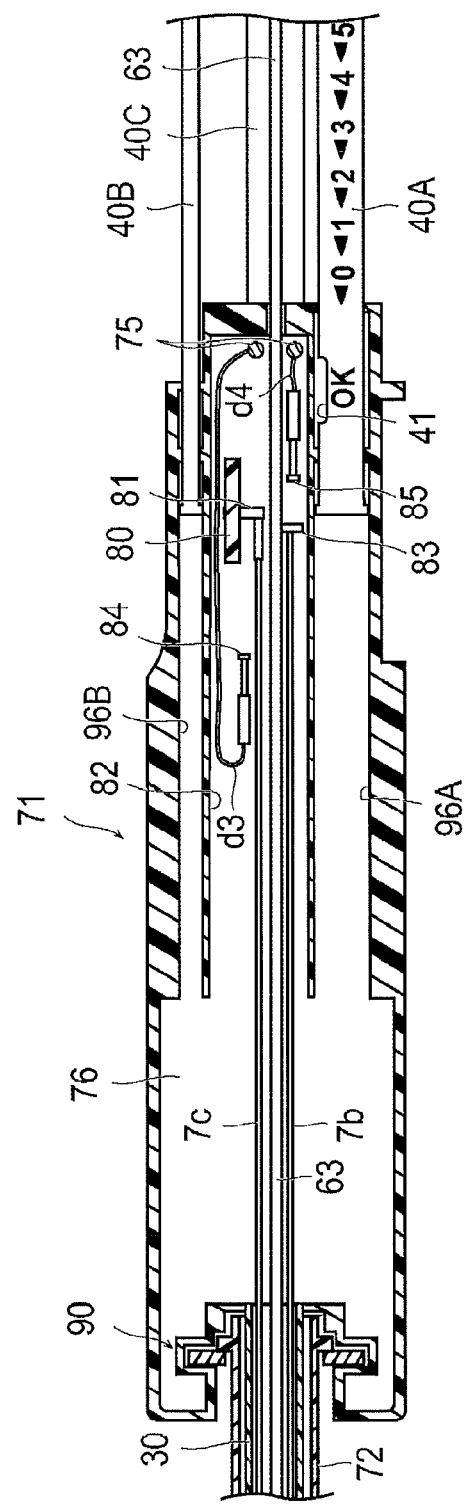
FIG. 5 is a cross-sectional view of the hand-side steering unit taken along a line 5-5 as shown in FIG. 2.

On the side surface (upper surface side) of the main body portion 71, a concave portion 77 is formed, as shown in FIG. 4 and the needle steering lever 78 slidably reciprocates within the lengthwise direction of the concave portion 77 (see outline arrow). As shown in FIG. 5, the needle steering lever 78 includes a bracket 80 which is inserted through a slit (not shown) formed at the main body portion 71 so as to protrude into an inner space 76 of the main body portion 71. The bracket 80 has interlocked therewith an L-shaped terminal 81 which is provided on the proximal side of the steering cord 7c for the sticking member 2. Therefore, when sliding the needle steering lever 78 (see FIG. 4) along the slit, the bracket 80 and the terminal 81 also slide, as shown in FIG. 5, along a guide groove 82 which is formed inside the main body portion 71 such that the sticking member 2 is advanced and retracted through movement of the steering cord 7c.

The main tube 63, as explained in detail below, passes through the main body portion 71 at approximately the center of the inner space 76. The proximal side of the main tube 63 is interlocked with the slide portion 100 by an adhesive agent or the like (see FIG. 9), and in accordance with the slide operation of the slide portion 100, the main tube also slides and is guided by the main body portion 71.

A terminal 83 is attached to the main tube 63 inside the inner space 76 in the vicinity of the right end, such that the terminal 83 also slides along with the sliding of the main tube 63. A steering cord 7b is connected to the terminal 83 and passes through a side portion of the main tube 63. At the movement termination end positions of these terminals 81, 83, contact members 84, 85 are provided which function as switches. As will be apparent to one skilled in the art, the electric system of the sticking member 2 and the electric system of the sandwich member 1 are insulated so as not to be conductive.

The contact members 84, 85 are connected to both electrodes of the input connector 75 by means of conductive wires d3, d4 and are disposed so as to contact terminals 81, 83, respectively, before reaching the movement-completion positions of the terminal 81, 83 which move along with the movement of the steering cord 7c for the sticking member 2 and the steering cord 7b for the sandwich member 1, respectively.

Figure 6:
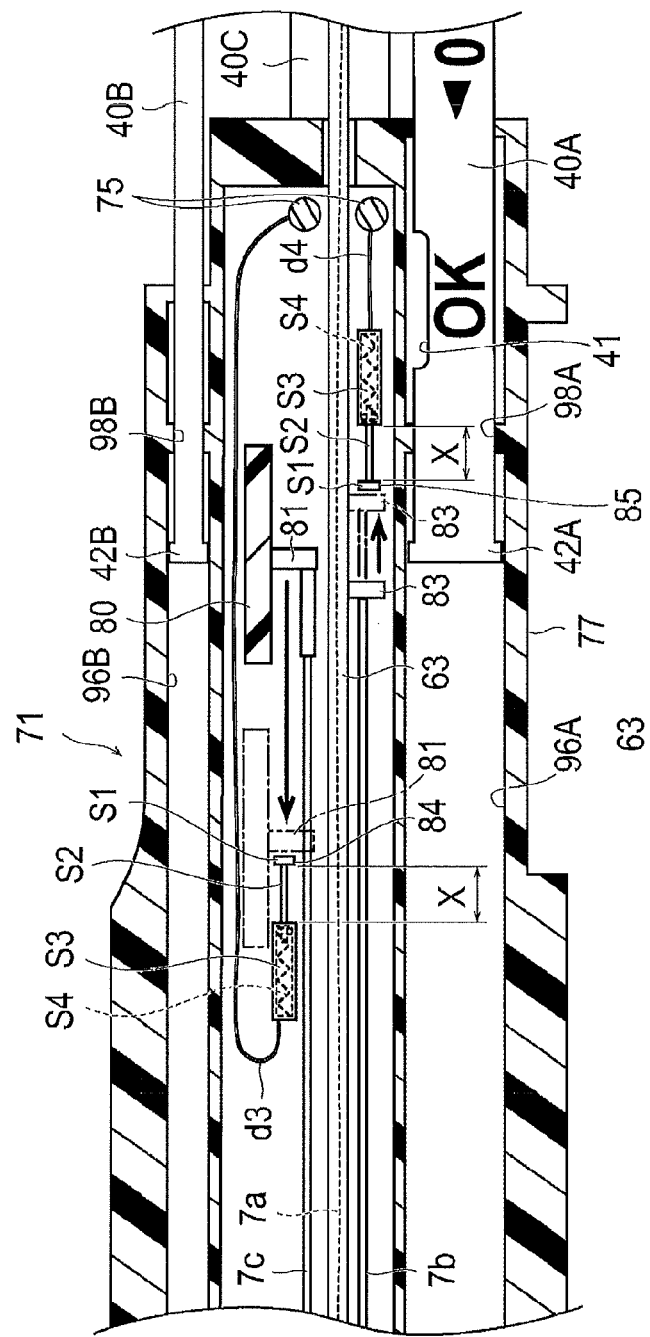
FIG. 6 is an enlarged cross-sectional view of the hand-side steering unit taken along a line 5-5 as shown in FIG. 2.

The contact members 84, 85 will now be explained in further detail. As shown in FIG. 6, the contact members 84, 85 include attaching portions S1 for contacting the terminals 81, 83; leg portions S2 protruding from the attaching portions S1; tube shaped collars S3 inside which protrusion ends of the leg portions S2 are housed; and springs S4 for springing or urging the leg portions S2 toward the outside thereof. Therefore, each attaching portion S1 is protruded by the spring S4 on a steady or continuous basis, but when it is pushed by the terminal 81, 83 it moves backward so that, as shown in the drawing, there is a conductable range X of a predetermined length.

By employing such a configuration, even if the sticking state of the sticking member 2 or the sandwiching state of the sandwich member 1 should vary because of a difference in the thickness and/or the shape of the foramen ovale valve M2 or the like depending on an individual person and the movement-completion positions of the terminals 81, 83 are thus different, the contact members 84, 85 still reliably contact with the terminals 81, 83 such that electrical conduction is possible and the reliability of the procedure is secured. In addition, it is possible to use an alternative mechanism having a construction in which the electric contact state is slidably formed, but in comparison with such a slide mechanism, the spring-biased contact between the contact members 84, 85 and the terminals 81, 83 is deemed more reliable, breakdown becomes less likely, and, with respect to the slide operation of the terminals 81, 83, the frictional resistance force becomes less and lighter.

However, it is not necessary for the pairs of the contact members 84, 85 and the terminals 81, 83 to all be in an elastic (spring-biased) contact state and it is acceptable if only one side thereof is in that state and the other side thereof is in a usual contact state. Alternatively, it is acceptable for both the sides thereof to be in a usual contact state without providing the pairs of the contact members 84, 85 and the terminals 81, 83.

Guide bars 40A, 40B are provided inside of grooves 96A, 96B inside the main body portion 71, and a guide bar 40C is provided inside of a groove which is not shown. As shown in FIG. 6, protrusion portions 42A, 42B for preventing disengagement with the grooves are provided at the ends of one side of the guide bars 40A, 40B and they stop the guide bars from sliding out of the grooves by abutting the stopper portions 98A, 98B provided in the grooves 96A, 96B, respectively.

The main steering rod 7a is a rod which is provided inside the main tube 63 and which has a function of assisting the operation of the clamping means K by being traction-operated in the axial direction, and it is configured so as to be rotatable by 360 degrees centering around the longitudinal axial line inside the main tube 63. If the main steering rod 7a is rotatable by 360 degrees, it is possible for the rod to be inserted through the foramen ovale O by inserting the distal end of the main steering rod 7a as far as possible in the vicinity of the foramen ovale O and by then positionally displacing the rod in a rotational manner. According to this result, even if the foramen ovale O is deformed in some manner, it is possible for the distal end of the device to be inserted through the foramen ovale O regardless of the deformed shape thereof. The procedure can thus be performed easily and quickly.

Figure 8:
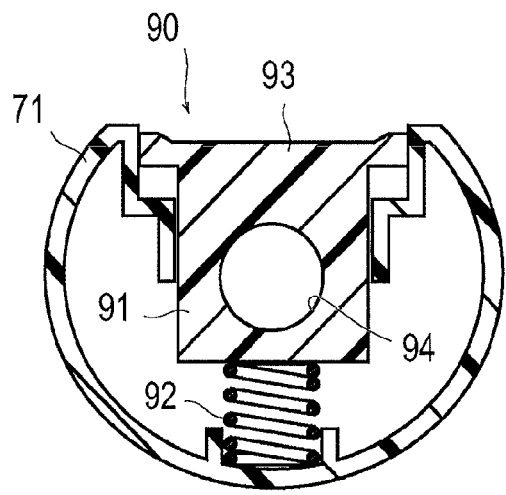
FIG. 8 is a cross-sectional view showing an interlock mechanism taken along a line 8-8 as shown in FIG. 4.

At the distal portion of the main body portion 71, a push button 93 for an interlock mechanism 90 is provided (see FIG. 2). The interlock mechanism 90 is a mechanism for simplifying detachment and attachment of a Y connector 72. With respect to the main body portion 71, while pushing down on the push button 93, a flange portion at the proximal portion of the Y connector 72 is fitted into an insertion hole formed in the main body portion 71 and the flange portion of the Y connector 72 engages with an engagement hole 94 of a slide member 91, as shown in FIG. 8. Then, the pressing force to the push button 93 is released such that the slide member 91 is sprung (returned to its original undepressed state) by a spring member 92, and the flange portion is maintained in position. By pushing down the push button 93 once again, it becomes possible for the Y connector 72 to be detached from the slide member 91. Hence, the Y connector is releasably attached.

Note that at the distal end of the hand-side steering unit 70, as shown in FIG. 2, it is preferable to provide a Y connector 72 into which a contrast agent or the like can be injected. In a case in which the Y connector 72 is not used, however, a guiding catheter 31 having a similar flange portion can be directly interlocked with the main body portion 71. One skilled in the art will appreciate that the Y connector 72 can be provided at an arbitrary position of the guiding catheter 31.

At the proximal portion of the main body portion 71, a connection hole 74 is provided corresponding to the exterior shape of the output connector 87, and inside this connection hole 74, an electrode terminal of the input connector 75 is disposed.

The guide bar 40A is arranged such that a portion of the lateral side thereof enters into the connection hole 74 and thus hinders insertion of the output connector 87 into the connection hole 74 and prevents connection of the output connector 87 with the input connector 75. Further, at another portion of the lateral side of the guide bar 40A a cutout portion 41 (connection adjusting unit), is formed and as shown in FIG. 7, the output connector 87 becomes connectable with the input connector 75 when this cutout portion 41 is aligned with the connection hole 74.

The guide bar 40A and the main tube 63 are both fixed to the slide portion 100, so that when, as shown in FIGS. 12A and 12B, the slide portion 100 is moved backward in the proximal direction, as shown by the dashed-dotted lines in FIG. 6, the main tube 63 slides inside the main body portion 71 together with the guide bar 40A, and the terminal 83 fixed on the main tube 63 contacts with the contact member 85, and the sandwich member 1 and the input connector 75 are there electrically connected. The contact member 85 has a conductable range X of a predetermined length as mentioned above. The cutout portion 41 is thus formed on the guide bar 40A with a given size that makes it possible for the output connector 87 to be connected to the input connector 75 within this conductable range X.

Figure 7:
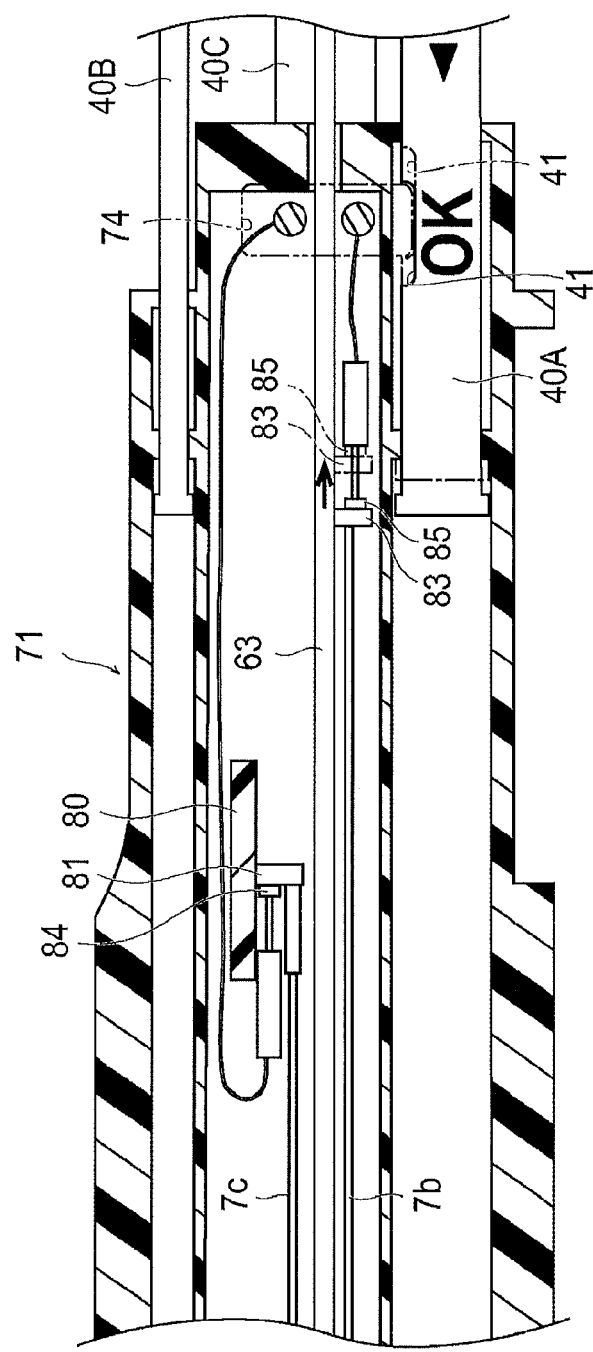
FIG. 7 is an enlarged cross-sectional view of the hand-side steering unit shown in an operative position when a slide portion is moved backward.

More specifically, in FIG. 7, the terminal 83, the contact member 85 and the cutout portion 41 which are shown by dashed-dotted lines indicate a transition from a state in which the terminal 83 and the contact member 85 are first contacted by moving the slide portion 100 backward (see terminal 83, contact member 85 and cutout portion 41 which are shown by solid lines in FIG. 7) to a state in which the slide portion 100 is further moved backward as much as the conductable range X, such that within this range, the cutout portion 41 coincides with the connection hole 74 and the guide bar 40A does not protrude into the connection hole 74 and the output connector 87 (see FIG. 1) is connectable to the input connector 75 without being hindered by the guide bar 40A.

Owing to such a construction as described above, the connection between the energy supply means 20 and the input connector 75 can be carried out only after the sandwiching of the biological tissue M is completed. The safety of the procedure is thereby increased regardless of the physical or mental state of the operator. In other words, the connection adjusting unit has a size allowing connection between the input connector and the output connector only when the slide portion lies in a relative position within a certain range with respect to the main body portion, and it improves the safety of the device by suppressing careless electric energy application while responding flexibly to biological tissue which has individual differences.

As shown in FIG. 4, the main body portion 71 is provided with a window 73 which is disposed adjacent to the input connector 75. Further, on the guide bar 40A, an "OK" indicating portion H6 (see FIG. 6) is provided in the vicinity the cutout portion 41 and, in addition, numbers (1 to 5) are sequentially provided at a constant pitch together with triangle arrows.

When pulling-in and withdrawing the positioning hold means 60 into the inside of the catheter 30 by moving the slide portion 100 backward from the main body portion 71 (as described in greater detail below), the hand-side steering unit 70 is configured such that the numbers provided on the guide bar 40A appear at the window 73 sequentially so as to be counted down and finally, the "OK" indicating portion H6 appears at the window 73. When the terminal 83 contacts with the contact member 85 within the conductable range X, the entirety of the "OK" indicating portion H6 (or other indicating indicia) appears at the window 73. In a case of deviating from the conductable range X, the entire "OK" indicating portion H6 will not appear within the window 73.

Figure 9:
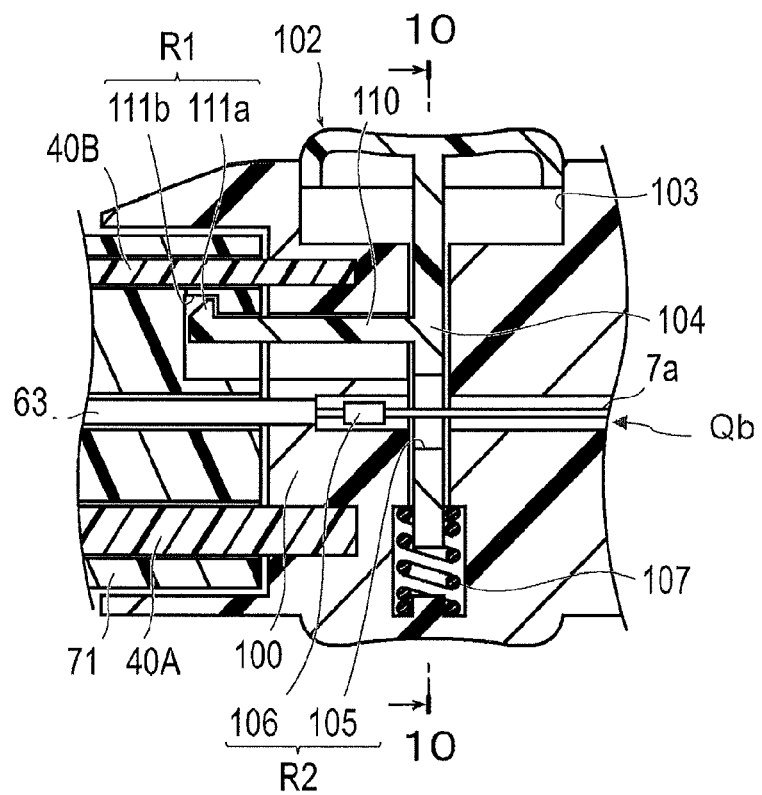
FIG. 9 is a cross-sectional view of a lock and unlock mechanism portion taken along a line 9-9 as shown in FIG. 4.
Figure 10:
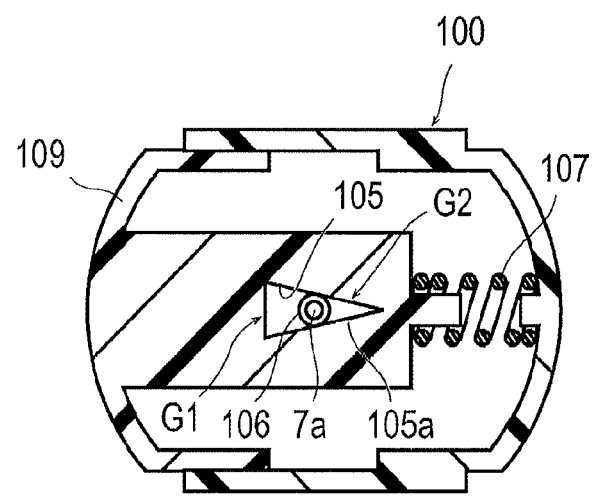
FIG. 10 is a cross-sectional view taken along a line 10-10 as shown in FIG. 9.

The lock and unlock mechanism 102 shown in FIGS. 9 and 10 is provided at the slide portion 100. By pressing the pusher piece 109, the mechanism locks and unlocks the slide movement of the slide portion 100 and simultaneously, locks and unlocks the axial direction movement of the main steering rod 7a.

The lock and unlock mechanism 102 includes a first lock portion R1 for the slide portion 100, which interlocks the slide portion 100 and the main body portion 71 by sliding an operation member 104 and thus makes the slide movement possible by releasing the lock; and a second lock portion R2 for the main steering rod, which temporarily stops the advancement and retraction steering in the axial line direction of the main steering rod 7a when the positioning hold means 60 provided at the distal portion of the main steering rod 7a holds or positions the biological tissue M.

The first lock portion R1 includes an operation member 104 that is freely slidable inside a slide hole 103 which is formed at the slide portion 100, and a restricting rod 110 which is integral with the operation member 104 and which restricts the movement of the slide portion 100 with respect to the main body portion 71. Reference numeral 107 in FIGS. 9 and 10 is used to indicate a spring.

The restricting rod 110 is provided with an engagement protrusion 111a at the distal end thereof, which is engaged with an engagement concave portion 111b of the main body portion 71 so that, when the operation member 104 is pressed, the engagement between the engagement protrusion 111a and the engagement concave portion 111b is released and it becomes possible for the slide portion 100 to slide with respect to the main body portion 71. Therefore, if the slide portion 100 is operated backwards, it is possible to operate the sandwich member 1 adjacently with respect to the sticking member 2 through the steering cord 7b. In addition, the pressing of the operation member 104 causes the second lock portion R2 to be released.

By linking the release of the first lock portion R1 and the release of the second lock portion R2 by operating the pusher piece 109 and the operation member 104 in this manner, it is possible to link the storing operation of the sandwich member 1 into the inside of the catheter and the operation for reliably setting the main, steering rod 7a into a straight shape when pulling out the long main steering rod 7a out from the left atrium side. It is thus possible to prevent a traction operation in which the main steering rod 7a is curved and/or a moving-back operation of the sandwich member 1 when it is still in a sandwiching state, and thereby preventing potential damage or fracture to the biological tissue M.

On the other hand, the second lock portion R2 for the main steering rod 7a includes a locking portion 105 formed at the operation member 104 and a large diameter portion 106 formed at the main steering rod 7a. With respect to the second lock portion R2, in order to temporarily stop the advancement and retraction steering of the main steering rod 7a in the axial line direction, the locking portion 105 provided at the operation member 104 is formed as a wedge-shaped through-hole having a wide width portion G1 and a narrow width portion G2. If the wedge-shaped through-hole is employed in this manner, just by moving the main steering rod 7a inside the through-hole, the engagement of the large diameter portion 106 becomes stronger and, even if pressurizing means or the like is not provided separately, it is possible to hold the main steering rod 7a in the fixing position and thereby carry out the procedure more easily, safely and reliably.

In performing a procedure, a stick (or piercing) operation by the sticking member 2 is carried out after the positioning hold means 60 carries out the holding and/or positioning of the biological tissue M, and the holding and/or the positioning of the biological tissue M has been carried out by exerting traction on the main steering rod 7a. Even if the holding and/or the positioning of the biological tissue M is carried out by exerting traction on the main steering rod 7a, it is not possible to carry out the stick operation if the holding state and/or the positioning state are/is not maintained. Therefore, if the second lock portion R2 engages the large diameter portion 106 with the locking portion 105 (depending on the situation, entrance edge portion 105a of a through-hole) when traction-steering the main steering rod 7a, the main steering rod 7a is temporarily brought into a locked state and the operator's hand grasping the main steering rod 7a is then released, it is still possible to maintain the holding state and/or the positioning state and to independently carry out only the sticking operation by the sticking member 2.

Also, with the second lock portion R2, it is possible to increase the usability of the steering depending on the position at which the large diameter portion 106 is provided. For example, in the case of carrying out traction of the main steering rod 7a in the direction of being pulled out from the slide portion 100, if the large diameter portion 106 is pressed into the locking portion 105 and is locked at the position where the pulling-out is stopped, it is possible to lock the main steering rod 7a in a hold state of the hold portion 62 and to maintain the hold state. If the lock is released, the distal portion of the main steering rod 7a becomes straight in shape automatically by the elasticity of the elastic wires 66, 67 in the hold portion 62 and the hold state of the foramen ovale valve M2 can be easily released.

The energy supply means 20 shown in FIG. 1 is a means for supplying electric energy to the clamping means K as generally known in the art, so a detailed explanation thereof will be omitted From a viewpoint of ease of control, it is preferable to employ electrical means regardless of direct current power source or alternate current power source. However, energy supply means 20 is not limited only to this and it is possible to employ any kind of means if it is capable of supplying energy by which the foramen ovale valve M2 and the atrial septum secundum M1 sandwiched by the clamping means K can be fused by using heat and if it can be pressed and bonded by adhesive factors such as collagen, elastin and the like. For example, it is also possible to use ultrasound, laser, microwave or high frequency wave and the like.

The positioning hold means 60, as shown in FIG. 2, generally includes a positioning portion 61 for positioning the sticking member 2 with respect to the foramen ovale O and a hold portion 62 for holding the foramen ovale valve M2 in a non-retractable manner with respect to the sticking direction of the sticking member 2. Normally, the positioning hold means 60 is housed inside the guiding catheter 31, but at the time of use, it is pushed out from the guiding catheter 31 by steering the main steering rod 7a and the main tube 63 as shown in the drawing.

More particularly, in the center lumen L5 formed at the distal end tip 32, the main tube 63 is disposed together with the main operation rod 7a which is freely advanced and retracted in the axial direction inside the main tube 63. The main tube 63 is a tube whose proximal side is held fixedly at the slide portion 100 and which defines a center axis function of the disclosed device. The main tube 63 also reinforces the catheter 30 and provides a tube for pulling and withdrawing the positioning hold means 60 into the catheter 30. The main steering rod 7a passes through the inside of the main tube 63 from the distal end of the catheter 30, passes through an internal path of the slide portion 100 and protrudes from the rear end thereof.

At the distal portion of the main tube 63, the positioning portion 61 of the positioning hold means 60 is provided. The positioning portion 61 is a portion for positioning the sticking member 2 with respect to the foramen ovale O and is, as shown in FIG. 2, comprised of a pair of first elastic wires 66 which are operatively expanded and contracted by the steering of the main operation rod 7a. The proximal end of the first elastic wire 66 is mounted on the outer surface of the main tube 63 and the distal end thereof is mounted on the proximal side of the intermediate sleeve body 64, inside of which the main steering rod 7a is inserted.

The positioning portion 61 moves the main operation rod 7a so as to protrude from the distal end of the main tube 63 and displaces the first elastic wires 66 outward by making the proximal end attached to the main tube 63 serve as a supporting point depending on the operation for advancing and retracting the main operation rod 7a in the axis direction. It also depresses the inner edge of the foramen ovale O with approximately equal elastic force from the respective first elastic wires 66 and aligns the sticking member 2 with respect to the foramen ovale O. In other words, the sticking member 2 positioned between both the first elastic wires 66 is positioned at a central portion of the foramen ovale O.

On the other hand, the hold portion 62 is a portion which holds the sticking member 2 from the rear surface side so as to stick the foramen ovale valve M2 easily and includes, as shown in FIG. 2, a bump member 68 provided at the distal portion of the main steering rod 7a, a distal end sleeve body 65 and a pair of second elastic wires 67 by which the intermediate sleeve body 64 and the distal end sleeve body 65 are interlocked. The bump member 68 is fixed on the distal end of the main steering rod 7a. The main steering rod 7a is inserted through the inside of the distal end sleeve body 65 and the intermediate sleeve body 64. The proximal end of the second elastic wire 67 is welded to the distal end of the intermediate sleeve body 64 and the distal end of the second elastic wire 67 is welded to the distal end sleeve body 65.

The second elastic wire 67 and the bump member 68 for interlocking the intermediate sleeve body 64, the distal end sleeve body 65 and both the sleeve bodies 64, 65 constitute a curving mechanism W which curves or bends the distal portion of the main steering rod 7a.

The curving mechanism W is a mechanism used for holding the foramen ovale valve M2. When the sticking member 2 sticks the foramen ovale valve M2, the sticking becomes easier if the thin foramen ovale valve M2 is held from the rear surface side thereof. Therefore, the curving mechanism W is configured such that the second elastic wire 67 is curved or bent between the bump member 68 and the distal side of the first elastic wire 66 by moving the main steering rod 7a backward in the axial direction and the foramen ovale valve M2 is held from the rear surface side by the bump member 68 and the distal end sleeve body 65. In other words, the curving mechanism W is configured such that the distal portion of the main steering rod 7a is curved or bent by making the distal side of the first elastic wire 66 mounted on the main tube 63 serve as a supporting point.

It is necessary for the curving mechanism W of the hold portion 62 to be configured so as to be curved and hold the foramen ovale valve M2 after the first elastic wire 66 of the positioning portion 61 aligns and positions the sticking member 2 with respect to the foramen ovale O. Thus it is necessary for the first elastic wire 66 to deform in advance of the second elastic wire 67, and therefore, in the exemplified embodiment described here, the elastic members are made with a different rigidity.

When the slide portion 100 is advanced and retracted with respect to the main body portion 71, it is possible for the main tube 63 fixed firmly to the slide portion 100 to be pulled into the inside of the lumen L5 in the center of the catheter 30 and along with this operation, it is possible to withdraw the entire positioning hold means 60 into the inside of the catheter 30 as well.

Next, an operation of this exemplified embodiment will be explained as follows.

The operator inserts an introducer (dilator and long sheath) from the femoral vein. The distal end of the long sheath is made to reach the left atrium L by way of the right atrium R and thereafter, the dilator is pulled out from the long sheath.

The pusher piece 109 of the first lock portion R1 in the lock and unlock mechanism 102 is squeezed and pressed inward on the slide portion 100, and the operation member 104 is lowered inside the slide hole 103 and the restriction of the restricting rod 110 is removed. Thus, the slide portion 100 obtains a movable state with respect to the main body portion 71. Note that a portion of the lateral side of the guide bar 40A enters into the connection hole 74, thereby hindering connection of the output connector 87 to the input connector 75 such that unexpected power supply from the energy supply means 20 is reliably suppressed and safety is secured.

When the slide portion 100 is moved backward with respect to the main body portion 71, the needle steering lever 78 is also simultaneously moved backward, and there is obtained a state in which the wire member portion 1b of the sandwich member 1, the sticking member 2 and the like are stored inside the catheter 30.

In this state, the catheter is inserted into the inside of the long sheath and is advanced as far as the left atrium L, passing through the femoral vein J and the right atrium R.

When the distal end of the catheter 30 reaches the left atrium L, the movement of the slide portion 100 has progressed with respect to the main body portion 71. Thus, the flat-plate portion 1a of the sandwich member 1 protrudes from the distal end of the catheter 30 due to steering of the steering cord 7b. Also, the main tube 63 is moved forward and concurrently, the pusher piece 109 of the lock and unlock mechanism 102 is pressed and a state is brought about in which the large diameter portion 106 of the main steering rod 7a does not abut the narrow width portion G2 of the through-hole 105 formed in the operation member 104, in other words, the second lock portion R2 is brought into an unlocked state and the main steering rod 7a is brought into a free state.

Then, from the distal end of the main tube 63, the distal end of the main steering rod 7a is protruded from the distal end sleeve body 65. It is possible for this protrusion state to be confirmed visibly from the outside (external to the living body) because an X-ray impermeable marker may be provided on the bump member 68.

The traction processes of the main steering rod are described below. (Note that in the drawing, the sequence of the processes is indicated by numbers with circles, but in the description below, they are indicated by numbers in parentheses.)

Figure 18A:
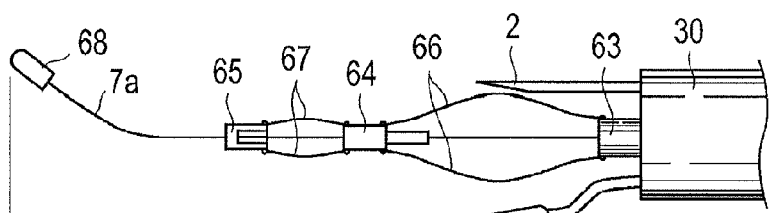
FIGS. 18A to 18D are schematic diagrams showing various operation states of the PFO closing device respectively.
Figure 18B:
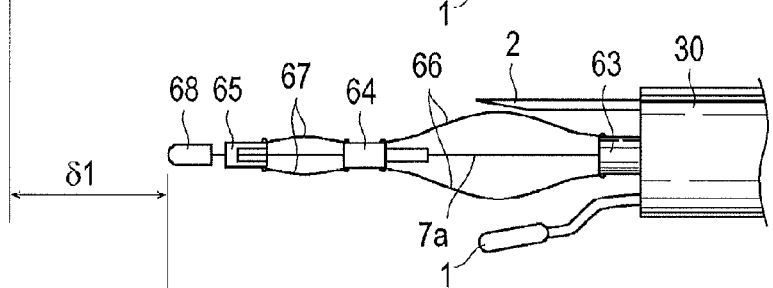

As shown in FIG. 4, at the indicating portion H1 of the rod traction process, there is applied an indication of exerting traction on the main steering rod 7a by showing fingers being pinched together with an indication of the number (1). In accordance with this indication, after confirming the distal end position of the main steering rod 7a, the operator makes, as shown in FIG. 18B, the main steering rod 7a move backward until the bump member 68 at the distal end of the main steering rod 7a abuts the distal end sleeve body 65 (the moveback amount is "δ1" in FIG. 18B).

When the main steering rod 7a is moved backward, the large diameter portion 106 is also moved backward. In the lock and unlock mechanism 102, the operation member 104 is biased upward by the spring force of the spring 107 (unless a pressing of the pusher piece 109 occurs) so that the main steering rod 7a is regularly compression-held between the narrow width portion G2 of the wedge-shaped through-hole 105 and the inner circumferential surface of the internal path Qb and therefore, it is possible, with respect to the movingback of the main steering rod 7a, to carry out the pulling operation smoothly. Thereafter, the main body portion 71 is steered and the second elastic wire 67, the sandwich member 1 and the sticking member 2 are positioned in the vicinity of the foramen ovale valve M2, and the entire hold portion 62 is inserted to the left atrium L side.

Figure 18C:
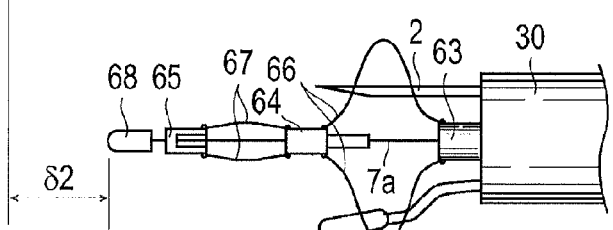

When the main steering rod 7a is moved further backward (the moving-back amount is "δ2" in FIG. 18C), this steering force of moving backward is transmitted to the first elastic wire 66 (whose proximal end is mounted on the main tube 63) by the main steering rod 7a passing through the bump member 68, the distal end sleeve body 65, the second elastic wire 67 and the intermediate sleeve body 64, The first elastic wire 66 is deformed protrusively into an arc shape toward the outward in the diameter direction as shown in FIG. 18C. However, at this point in time, the second elastic wire 67 is not deformed.

Based on this result, the first elastic wire 66 deforms while pressing and expanding the rim portion of the foramen ovale O, so that the sticking member 2 provided just near the first elastic wire 66 is aligned with respect to the foramen ovale O and the sticking member 2 is positioned at the center of the foramen ovale O.

Figure 15:
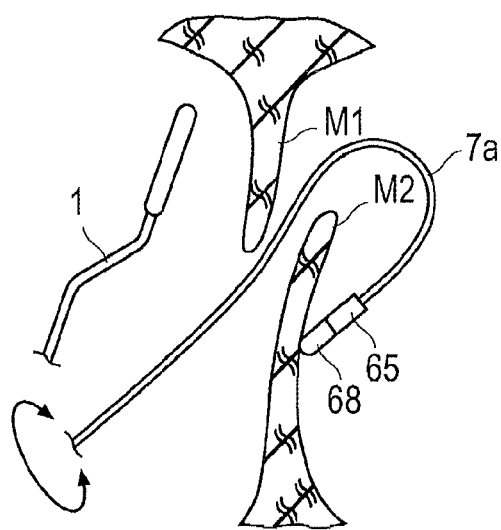
FIG. 15 is a cross-sectional schematic diagram in which a main steering rod is inserted into a foramen ovale.
Figure 18D:
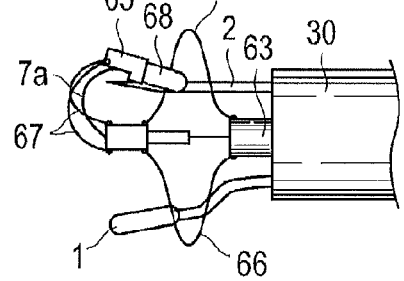

Steering rod 7a is steered further so as to move backward and when the rear end of the intermediate sleeve body 64 abuts the distal end of the main tube 63 as shown in FIG. 18D, the first elastic wire 66 does not deform much and the second elastic wire 67 on the distal side deforms protrusively in an arc shape toward the outward in the diameter direction by the steering force. According to this result, as shown in FIG. 15, the bump member 68 and the distal end sleeve body 65 curve in the inside of the left atrium L so as to approach to the sticking member 2, such that the bump member 68 and the distal end sleeve body 65 abut the surface on the left atrium side of the foramen ovale valve M2 and thus hold the same.

In the second lock portion R2 of the lock and unlock mechanism 102 shown in FIGS. 9 and 10, the large diameter portion 106 is pressed into the locking portion 105 which is a wedge-shaped through-hole and the main steering rod 7a is locked. According to this result, even if the operator releases a hand from the main steering rod 7a, the hold state is reliably maintained and the hold of the foramen ovale valve M2 is not loosened. It is therefore possible for the operator to make the needle steering lever 78 move with only a single hand.

Figure 16:
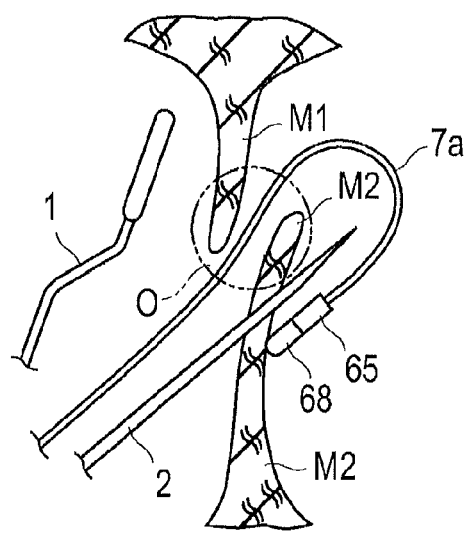
FIG. 16 is a cross-sectional schematic diagram in a state in which a foramen ovale valve is held and a sticking unit is stuck.

When the needle steering lever 78 is made to progress in the arrow direction (see FIG. 11), the sticking member 2 protrudes from the distal end of the catheter 30 due to steering of the steering cord 7c and, as shown in FIG. 16, the sticking member 2 is stuck into a predetermined position of the foramen ovale valve M2. There is no concern that sticking will not occur at the predetermined position due to a looseness of the holding of the foramen ovale valve M2.

When the sticking member 2 is moved toward the sticking direction, relative to the hand-side steering unit 70, as shown in FIG. 11B, an indication of the next moving direction and a number indicating the sequence of the operation process appear from the bottom surface thereof. By providing the same, the disclosed embodiment prevents an operator from forgetting to pull out the sticking member 2 after the sticking, and the reliability and safety of the procedure are thus increased.

The position of the sticking member 2 is set by the positioning hold portion 62, so that there is no concern of deviation from the desired position and also, when sticking the sticking member 2, the position of the sticking member 2 becomes an almost fixed position in relation to the foramen ovale valve M2. Therefore, the sticking operation becomes extremely easy for the operator.

When the sticking is completed, the slide portion 100 is made to progress further with respect to the main body portion 71. Thus, the flat-plate portion 1a of the sandwich member 1 protrudes from the distal end of the catheter 30 through the terminal 83 and the steering cord 7b.

Then, at the hand-side steering unit 70, as shown in FIG. 7, the terminal 81 mounted on the needle steering lever 78 progresses and contacts the member 84 such that an electrically conductive state is obtained between the sticking member 2 and the input connector 75.

When the flat-plate portion 1a comes to a position facing the atrial septum secundum M1, the slide portion 100 is moved backward from the main body portion 71 as shown in FIG. 12A. Even at this point in time, a portion of the guide bar 40A has entered into the connection hole 74, thereby hindering connection of the output connector 87 to the input connector 75, so that safety is secured.

Figure 17:
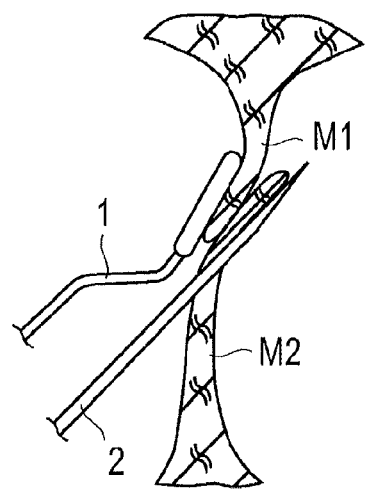
FIG. 17 is a cross-sectional schematic diagram in which a foramen ovale valve and an atrial septum secundum are sandwiched by a sticking unit and a sandwich member.

Due to the moving-back of the slide portion 100, the flat-plate portion 1a is also moved backward by the steering cord 7b shown in FIG. 2. The flat plate portion 1a is influenced by a force exerted when a bend portion 1c of the wire member portion 1b enters into the inside of the lumen of the distal end tip 32, and the flat-plate portion 1a is thereby displaced so as to approach the sticking member 2. As caused by this displacement, the flat-plate portion 1a presses the atrial septum secundum M1 toward the foramen ovale valve M2, in the thickness direction. In other words, since the positions of the M1 and M2 in the forward and backward direction in the operation state are fixed, a sandwiched state is obtained in which the atrial septum secundum M1 and the foramen ovale valve M2 exist between the sandwich member 1 and the sticking member 2, as shown in FIG. 17.

Figure 12:
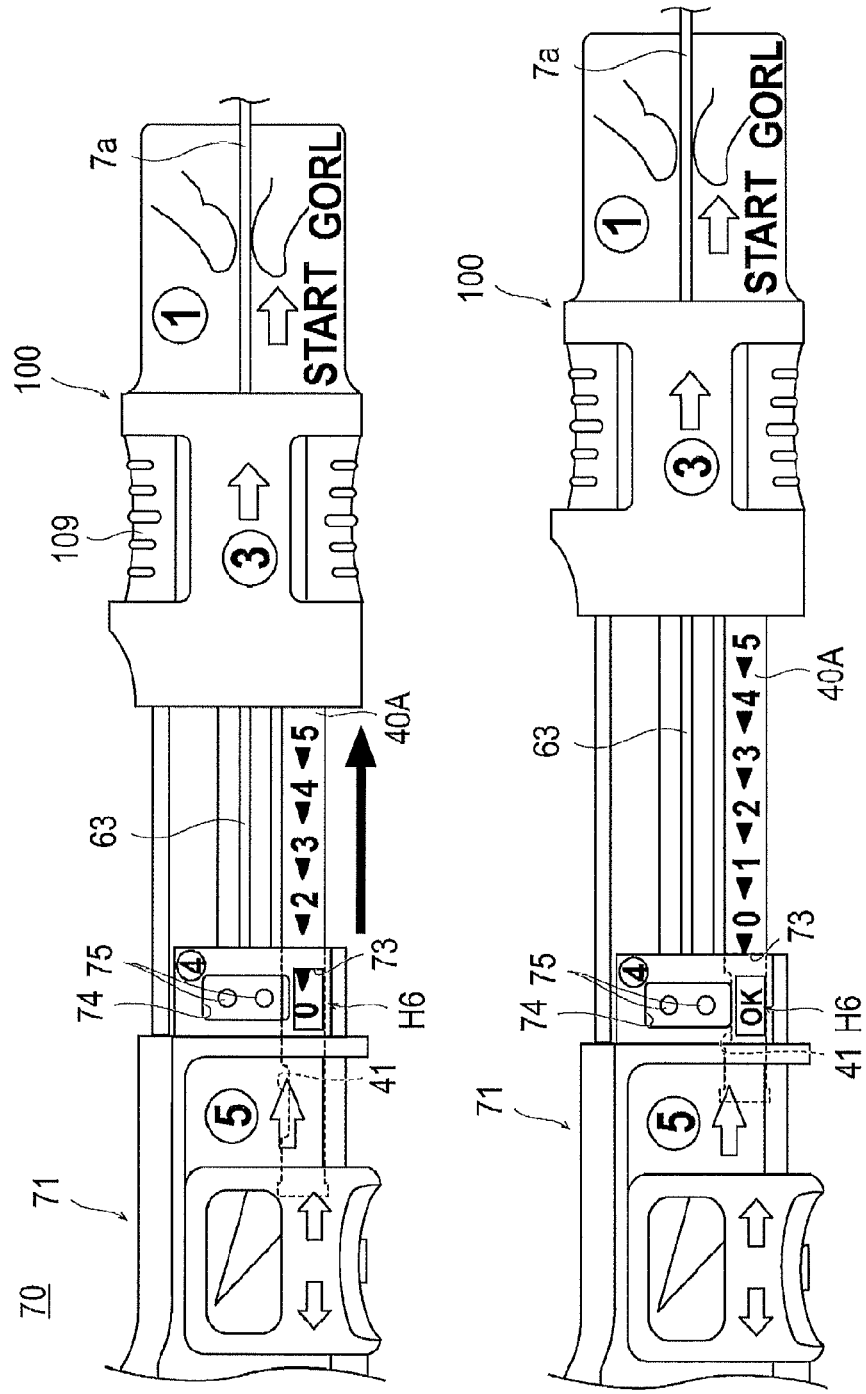

At this stage, in order to release the lock of the second lock portion R2 in the lock and unlock mechanism 102 shown in FIGS. 9, 10, the pusher piece 109 is pressed and the lock of the main steering rod 7a is released, the tension of the first elastic wire 66 and the second elastic wire 67 by the main steering rod 7a and the bump member 68 disappears, and the first elastic wire 66 and the second elastic wire 67 obtain a linearly extended state caused by their own elastic force. In this state, as shown in FIG. 12, when the slide portion 100 is steered so as to move backward, the whole positioning hold means 60 is withdrawn into the inside of the lumen L5 of the catheter 30 through the main tube 63. As shown in FIG. 12B, when the "OK" indicating portion H6 appears fully within the window 73, it can be understood that the withdrawal has terminated.

Further, in the hand-side steering unit 70, as shown in FIG. 7, the terminal 83 mounted on the main tube 63 also moves backward and contacts the member 85, and there is obtained an electrically conductive state between the sandwich member 1 and the input connector 75. The contact member 85 has a conductable range X and, within this conductable range X, the cutout portion 41 of the guide bar 40A also coincides and aligns with the connection hole 74 such that the output connector 87 becomes connectable with the input connector 75 for the first time. More specifically, due to the conductable range X, individual differences in the thickness and the shape of the foramen ovale valve M2 or the like are absorbed and, due to the existence of the cutout portion 41, there is obtained a state in which connection between the output connector 87 and the input connector 75 becomes possible only within the conductable range X.

In other words, it happens that with respect to the moving-back of the slide portion 100 at this stage, the sandwiching of the biological tissue M and the contact state of the terminal 83 and the contact member 85 are carried out all at once. Furthermore, the terminal 81 on the sticking member 2 side and the contact member 84 obtain an electrically conductable state in advance thereof, so that both of the sandwich member 1 and the sticking member 2 have obtained a state in which they can be supplied with electric energy.

Figure 13:
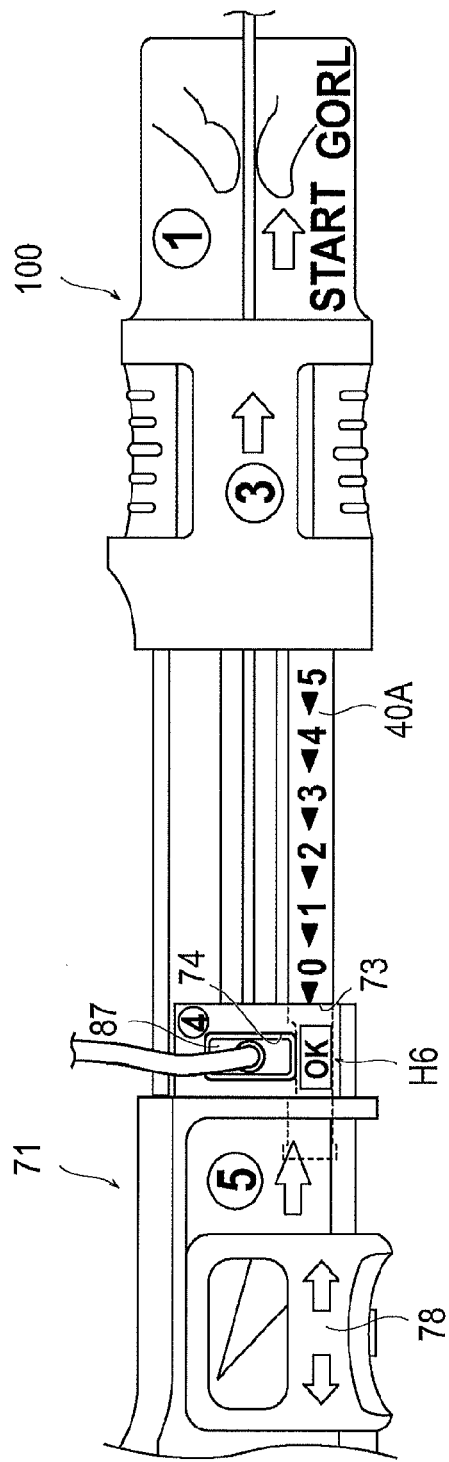
FIG. 13 is an enlarged plan view showing the hand-side steering unit in an operative position when an output connector is connected to an input connector of the hand-side steering unit.

Then, as shown in FIG. 12B, there exists a state in which the "OK" indicating portion H6 appears on the window 73, so that the operator can understand that the output connector 87 is allowed to be connected to the input connector 75 (see FIG. 13). When the output connector 87 is connected to the input connector 75, power supply from the energy supply means 20 is possible.

Note that in this state, the outer circumferential surface of the output connector 87 contacts the side surface of the cutout portion 41 of the guide bar 40A, and the sliding of the guide bar 40A is suppressed by a frictional force. More specifically, the output connector 87 and the cutout portion 41 function as fixing means by which the sandwich member 1 (heating unit) is fixed in a constant position and the movement of the sandwich member 1 after getting into an electrically conductible state is suppressed, and thereby maintains a desirable sandwiching state. It is not necessarily required to have a construction in which the outer circumferential surface of the output connector 87 contacts the side surface of the cutout portion 41 of the guide bar 40A.

Thereafter, by operating the switch SW, a predetermined electric energy controlled by the control unit 22 is supplied to the sandwich member 1 and the sticking member 2 through the operation cords 7b, 7c and the atrial septum secundum M1 and the foramen ovale valve M2 are heated.

Heating continues while maintaining the fusion temperature such that the tissues of the atrial septum secundum M1 and the foramen ovale valve M2 melt and are mutually fused by adhesive factors such as collagen, elastin or the like. The control unit 22 of the electric energy controls the output power to be low, thereby making attachment of thrombi difficult, so that even if a portion of the sandwich member 1 and the sticking member 2 is exposed in blood, attachment of the thrombus (thrombi) to the sandwich member 1 and the sticking member 2 can be prevented. The thrombi may become a cause of cerebral infarction, myocardial infarction or the like, so that by more reliably suppressing the occurrence of thrombi, it is possible to improve the safety of the device.

Figure 14:
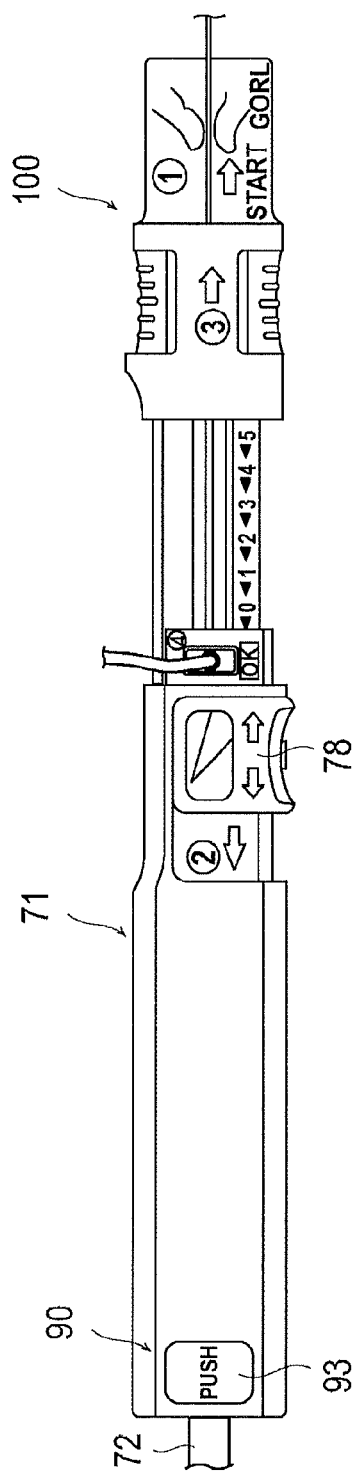
FIG. 14 is a plan view of the hand-side steering unit in an operative position when a needle steering lever is moved backward.

When the fusion is completed, the needle steering lever 78 shown in FIG. 13 is moved backward in accordance with the indication of an arrow indicated in the vicinity of the number (5) and is brought into the state of FIG. 14, and the sticking member 2 is housed inside the distal end tip 32. Thus, the terminal 81 which moves together with the needle steering lever 78 separates from the contact member 84 (see FIG. 5) and the electrically conductable state with respect to the clamping means K is released. Thereafter, the output connector 87 is removed from the input connector 75. Then, the push button 93 of the interlock mechanism 90 is pressed and by releasing the interlock between the Y connector 72 and the main body portion 71, the interlock between the guiding catheter 31 and the main body portion 71 is released such that when the main body portion 71 is moved backward so as to leave from the living body, the device is pulled out with the guiding catheter 31 serving as a guide. Thereafter, when the guiding catheter 31 is pulled out from the living body, the procedure is completed.

The disclosure here is not to be limited to only the exemplified embodiments mentioned above and it is possible to employ various modifications by persons skilled in the art within the technical ideas of the disclosed embodiments.

Figure 19:
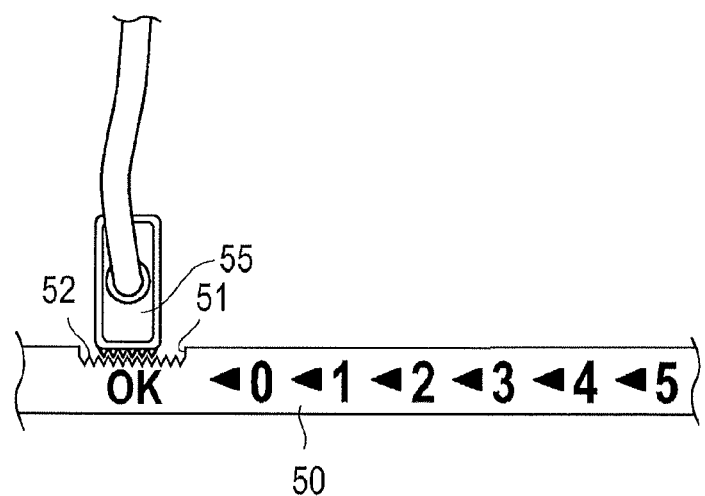
FIG. 19 is a plan view showing a guide bar and the output connector according to a modified embodiment disclosed here by way of example.

FIG. 19 shows another embodiment, by way of example, in which there is a notch 52 formed at a side surface of the cut portion 51 of the guide bar 50 and an output connector 55 is used having an exterior shape corresponding to the shape of this notch 52. If such a shape is employed, it becomes possible for the output connector 87 to be connected to the input connector 75 in an arbitrary position within the conductable range X of the contact member 85 and concurrently, after the output connector 87 is connected to the input connector 75, the guide bar 50 becomes unslidable, so that it is possible to reliably suppress the movement of the sandwich member 1 after obtaining an electrically conductable state and a desirable sandwiching position can be maintained. More specifically, the notch 52 functions as fixing means by which the slide portion 100 is fixed with respect to the main body portion 71, there being no limitation on the configuration thereof as long as the function as the fixing means is achieved by a mechanism in which the output connector 87 and the guide bar 50 contact each other.

Also, the guide bar 40A in this exemplified embodiment is fixed to the slide portion 100 on the proximal side and slides with respect to the main body portion 71. It is also possible, however, to have a construction in which the guide bar 40A is fixed to the main body portion 71 on the distal side and slides with respect to the slide portion 100. Also, it is possible for the input connector 75 to be provided at the slide portion 100, rather than at the main body portion 71.

Further, by way of example, for the connection adjusting unit which makes connection between the output connector 87 and the input connector 75 possible, instead of the cutout portion 41 formed as a notch or gap at the edge of the guide bar 40A, it is also possible to apply a through-hole which passes through the guide bar 40A.

Still further, by way of example, if the connection of the output connector 87 to the input connector 75 can be controlled by the guide bar 40A (guide unit) including the cutout portion 41 (or through-hole), it is possible that the connection hole 74 corresponding to the exterior shape of the output connector 87 is not necessary.

Also, with respect to the output connector 87 and the input connector 75, if they are connectable electrically, embodiments thereof are not limited.

Figure 20:
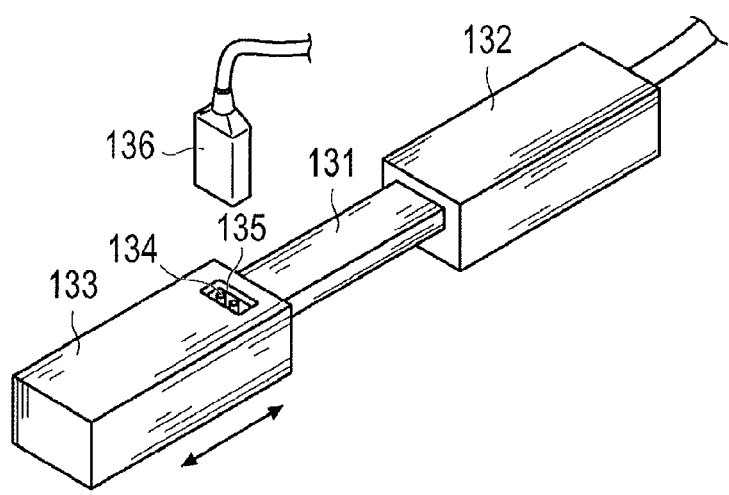
FIG. 20 is a perspective view showing another embodiment disclosed here by way of example.

FIG. 20 shows a schematic view of another embodiment disclosed here by way of example, in which a guide bar 131 is fixed to a main body portion 132 (or slide portion) and is slidable inside a slide portion 133 (or main body portion), and an input connector 134 is disposed on the guide bar 131 (guide unit). At the slide portion 133, a connection window 135 (connection adjusting unit) is provided in the form of a through-hole (or notch) which exposes the guide bar 131 slidingly disposed therein. The connection window 135 is disposed to coincide with the input connector 134 of the guide bar 131 when the heating unit is moved to the position at which the biological tissue is heatable after the slide portion 133 is advanced and retracted with respect to the main body portion 132. By employing such a construction, when the heating unit is moved to the position at which the biological tissue is heatable, it is possible to obtain a state in which the output connector 136 is connected with the input connector 134 through the connection window 135 and electric energy can be supplied to the heating unit.

Figure 21:
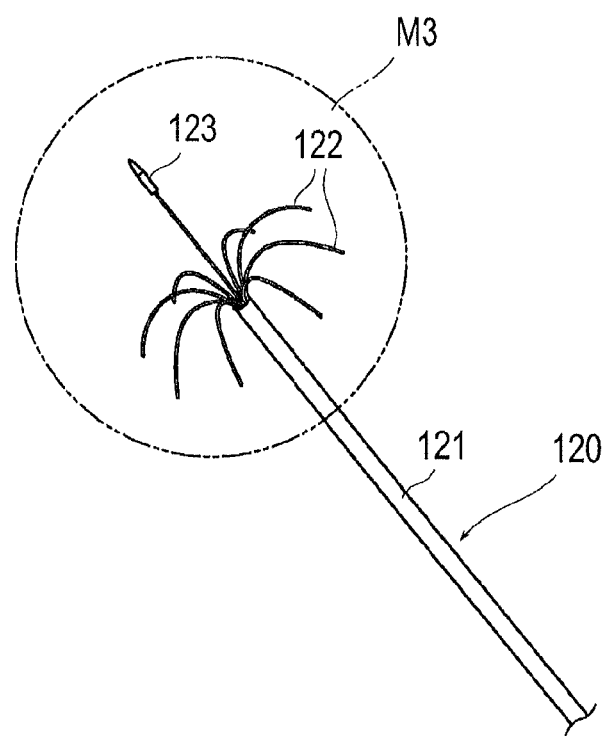
FIG. 21 is a perspective view showing still another embodiment disclosed here by way of example.

Also, in the embodiment disclosed herein, it was explained with respect to a device used for the treatment for closing the defect of the PFO, but the disclosed embodiment is not to be limited only by this device and one skilled in the art will recognize that it is also usable in a case of closing a path-shaped defect such as a left-atrial-appendage (Left Atrial Appendage) closing device or in a case in which a biological tissue M at a predetermined region is thermally necrotized. In addition, as shown in FIG. 21, the disclosure can also be applied to a medical device 120 or the like which is provided with a plurality of electrodes 122, protruding so as to be opened outward from the lumen inside the catheter 121, and an excision probe 123, and which applies electric energy from the electrode 122 after the electrodes 122 are protruded and opened outward inside a biological tissue such, for example, as a liver tissue M3 and the like.

The medical device according to the above-described embodiments has a high safety factor in that it is possible to lower the possibility of the electric energy being carelessly applied.

The detailed description above describes features and aspects of examples of embodiments of a medical device. The present invention is not limited, however, to the precise embodiments and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A medical device comprising a heating unit provided on a distal side of a catheter to heat a biological tissue and a hand-side steering unit provided at a proximal side of the catheter to steer advancement and retraction operations with respect to the catheter at the heating unit;
    wherein the hand-side steering unit comprises:
        a main body portion interlockable with the catheter;
        a slide portion which is interlockable with the heating unit and which is movable so as to approach and move backwards with respect to the main body portion;
        a guide unit movably interlocked with one of the main body portion and the slide portion and fixed secured on the other one of the main body portion and the slide portion;
        an input connector provided at one of the main body portion, the slide portion and the guide unit, the input connector being electrically connected with the heating unit, and connectable with which an output connector, for supplying electric energy to the heating unit;
        one of the main body portion, the slide portion and the guide unit being disposed for hindering connection between the input connector and the output connector, said one of the main body portion, the slide portion or the guide unit which is disposed for hindering connection between the input connector and the output connector being different from said one of the main body portion, the slide portion and the guide unit which is provided with the input connector; and
        a connection adjusting unit for enabling connection between the input connector and the output connector by moving the slide portion with respect to the main body portion when the heating unit is moved to a position at which the biological tissue is heatable.

2. The medical device according to claim 1, wherein the connection adjusting unit has a size allowing connection between the input connector and the output connector when the slide portion lies in a relative position within a certain range with respect to the main body portion.

3. The medical device according to claim 1, wherein at the main body portion, at the slide portion or at the guide unit, a switch is provided for carrying out electrical connection or release between the heating unit and the input connector by the movement of the slide portion to a predetermined position and, corresponding to the predetermined position of the slide portion at which electrical connection is made by the switch, the connection adjusting unit is configured such that the connection between the input connector and the output connector becomes possible.

4. The medical device according to claim 1, further comprising fixing means for fixing the movement of the slide portion with respect to the main body portion, said fixing means including the connection adjusting unit and the output connector frictionally engaging with each other when the output connector is connected to the input connector.

5. The medical device according to claim 1, wherein the guide unit includes an indicating portion having a notification to coincide with a predetermined position of the main body portion or of the slide portion in a state in which connection between the input connector and the output connector is possible.

6. The medical device according to claim 1, wherein said connection adjusting unit comprises a notch or a through-hole.

7. The medical device according to claim 1, wherein the heating unit comprises a clamping means for clamping biological tissue.

8. The medical device according to claim 7, wherein the clamping means comprises a flat plate sandwich member and a sticking member, both of which define electrodes.

9. A medical device for heat treating a living body comprising:
    a catheter defining an interior lumen;
    at least one electrode extending through the lumen of the catheter and protruding at a distal side thereof;
    a steering unit provided at a proximal side of said catheter for controlling advancement and retraction operations of said at least one electrode, said steering unit comprising:
        a main body portion;
        a slide portion slidably disposed relative to said main body portion; and
        an input connector;
    an output connector connectable with said input connector for supplying electric energy to said at least one electrode;
    means for hindering connection between said input connector and said output connector;
    a connection adjusting unit for enabling connection between said input connector and said output connector;

wherein said slide portion is configured to be movably positioned relative to said main body portion to a predetermined position indicative of said at least one electrode being positioned for heating relative to biological tissue;

wherein, only when said slide portion is in said predetermined position, said connection adjusting unit enables connection between said input connector and said output connector, thereby permitting electric energy to be supplied to said at least one electrode.

10. The medical device according to claim 9, wherein said steering unit includes a window for viewing an indicating indicia, the indicating indicia being fully visible within said window only when said slide portion is in said predetermined position indicative of said at least one electrode being positioned for heating relative to biological tissue.

11. The medical device according to claim 9, wherein said input connector is disposed within said main body portion and said main body portion includes a connection opening, said output connector being connectable with said input connector through said connection opening.

12. The medical device according to claim 11, wherein said means for hindering connection between said input connector and said output connector includes a guide unit, said guide unit blocking at least a portion of said connection opening such that said output connector is not connectable with said input connector.

13. The medical device according to claim 12, wherein said connection adjusting unit for enabling connection between said input connector and said output connector includes a gap in said guide unit such that said connection opening is not blocked when said gap is aligned with said connection opening.

14. The medical device according to claim 13, wherein said gap comprises a notch in a side of said guide unit or a through-hole in said guide unit.

15. The medical device according to claim 9, wherein said slide portion operates to steer the at least one electrode through forward and rearward movement relative to the main body portion.

16. The medical device according to claim 15, wherein said at least one electrode comprises a first electrode and a second electrode, said slide portion steering said first electrode, and wherein said steering unit further comprises a steering lever for steering said second electrode.

17. The medical device according to claim 9, wherein said steering unit includes a plurality of indicating portions providing graphic indications, numbers and/or arrows of movement directions corresponding to a predetermined sequence of processes to be followed by an operator.

18. A method for heat-treating a living body comprising:
providing a medical device comprising a catheter having an interior lumen, at least a first electrode, a second electrode and a positioning hold means extending through the lumen of the catheter, a steering unit provided at a proximal side of the catheter for controlling advancement and retraction operations of the first and second electrodes, wherein the steering unit comprises a main body portion, a slide portion slidably disposed relative to the main body portion, and an input connector; and an output connector connectable with the input connector for supplying energy to first and second electrodes;

inserting the catheter into a living body to a target site;
extending the first electrode from the catheter;
extending the positioning hold means from the catheter to position and hold the biological tissue;
extending the second electrode from the catheter and steering the second electrode to contact the biological tissue;
sliding the slide portion rearwardly relative to the main body portion so as to steer the first electrode into contact with the biological tissue such that the biological tissue is disposed between the first and second electrodes;
sliding the slide portion further rearwardly relative to the main body portion so that the positioning hold means is withdrawn inside the catheter;
visually observing an indicating indicia confirming withdrawal of the positioning hold means inside the catheter;
connecting the output connector with the input connector such that energy is supplied to the first and second electrodes, thereby heat-treating the biological tissue.

19. The method according to claim 18, further comprising, after connecting the output connector with the input connector, operating a switch such that a predetermined energy is supplied to the first and second electrodes.

* * * * *